(12) United States Patent
Wang (10) Patent No.: US 10,548,693 B2
(45) Date of Patent: Feb. 4, 2020

(54) DRILL FOR IMPLANT SURGERY

(75) Inventor: Je-Won Wang, Daejeon (KR)

(73) Assignee: Je Won Wang, Daejeon (KR)

( * ) Notice: Subject to any disclaimer, the term of this patent is extended or adjusted under 35 U.S.C. 154(b) by 0 days.

(21) Appl. No.: 14/006,200

(22) PCT Filed: Mar. 20, 2012

(86) PCT No.: PCT/KR2012/001985
§ 371 (c)(1),
(2), (4) Date: Nov. 11, 2013

(87) PCT Pub. No.: WO2012/128537
PCT Pub. Date: Sep. 27, 2012

(65) Prior Publication Data
US 2014/0065573 A1 Mar. 6, 2014

(30) Foreign Application Priority Data

Mar. 22, 2011 (KR) .......................... 10-2011-0025532

(51) Int. Cl.
 *A61C 8/00* (2006.01)
 *A61C 3/02* (2006.01)
(52) U.S. Cl.
 CPC .............. *A61C 8/0089* (2013.01); *A61C 3/02* (2013.01)
(58) Field of Classification Search
 CPC ......... A61C 3/02; A61C 8/0089; A61C 5/023; A61B 17/1615; A61B 17/1635; A61B 17/1673; A61B 17/1637
 USPC ......................................... 433/165–166, 224
 See application file for complete search history.

(56) References Cited

U.S. PATENT DOCUMENTS

| 1,123,730 | A |   | 1/1915  | Greenfield |
| 1,480,730 | A | * | 1/1924  | Lentz ............................... 433/75 |
| 3,892,117 | A | * | 7/1975  | Nelson ........................ 72/370.13 |
| 4,431,416 | A | * | 2/1984  | Niznick ......................... 433/174 |
| 4,820,156 | A |   | 4/1989  | Ross |
| 5,259,398 | A | * | 11/1993 | Vrespa .................. A61B 17/863 |
|           |   |   |         | 128/898 |
| 5,366,374 | A | * | 11/1994 | Vlassis ......................... 433/165 |
| 5,782,636 | A |   | 7/1998  | Armstrong et al. |
| 5,908,423 | A | * | 6/1999  | Kashuba et al. ................ 606/80 |

(Continued)

FOREIGN PATENT DOCUMENTS

| EP | 2 135 568 A3 | 5/2010 |
| KR | 10-2010-0088640 A | 8/2010 |

OTHER PUBLICATIONS

Communication dated Dec. 18, 2018, issued by the Indian Patent Office in counterpart Indian Patent Application No. 3063/KOLNP/2013.

*Primary Examiner* — Cris L. Rodriguez
*Assistant Examiner* — Hao D Mai
(74) *Attorney, Agent, or Firm* — Sughrue Mion, PLLC (57) ABSTRACT

Disclosed is a drill for implant surgery drill for implant surgery. The drill includes a drill connecting part having a drill top portion formed at one side of the top portion thereof, a drill fixing groove formed on the lower portion of the drill top portion, and a drill connecting body formed on the lower portion of the drill fixing groove; and a drilling part disposed on the underside of the drill connecting part and having a cylindrical shape in such a manner as to be small in diameter toward the lower portion thereof and to have a space portion formed at the inside thereof.

1 Claim, 5 Drawing Sheets

(56) References Cited

U.S. PATENT DOCUMENTS

| | | | |
|---|---|---|---|
| 5,951,561 A * | 9/1999 | Pepper et al. | 606/80 |
| 6,193,722 B1 * | 2/2001 | Zech | A61B 17/1637 |
| | | | 606/79 |
| 6,419,490 B1 * | 7/2002 | Kitchings Weathers, Jr. | |
| | | | 433/165 |
| 6,517,581 B2 * | 2/2003 | Blamey | 623/22.12 |
| 7,074,224 B2 * | 7/2006 | Daniels et al. | 606/80 |
| D644,327 S * | 8/2011 | Singh | D24/146 |
| 8,438,950 B2 * | 5/2013 | Courvoisier | 76/115 |
| 8,523,866 B2 * | 9/2013 | Sidebotham | A61B 17/1617 |
| | | | 606/80 |
| 9,782,196 B2 * | 10/2017 | Bradica | A61B 17/1635 |
| 2004/0267266 A1 * | 12/2004 | Daniels et al. | 606/80 |
| 2006/0111724 A1 * | 5/2006 | Yeung Wai Ping | |
| | | | A61B 17/1635 |
| | | | 606/80 |
| 2006/0217753 A1 * | 9/2006 | Bradica | A61B 17/1635 |
| | | | 606/184 |
| 2008/0195104 A1 * | 8/2008 | Sidebotham | A61B 17/1617 |
| | | | 606/80 |
| 2009/0274996 A1 | 11/2009 | Miller | |
| 2010/0228255 A1 | 9/2010 | Anitua | |
| 2013/0260334 A1 * | 10/2013 | Pernot et al. | 433/81 |

* cited by examiner

DRILL FOR IMPLANT SURGERY

CROSS REFERENCE TO RELATED APPLICATIONS

This application is a National Stage of International Application No. PCT/KR2012/001985 filed Mar. 20, 2012, claiming priority based on Korean Patent Application No. 10-2011-0025532, filed Mar. 22, 2011, the contents of all of which are incorporated herein by reference in their entirety.

TECHNICAL FIELD

The present invention relates to a drill for implant surgery that has a coupling structure to a handpiece for implant surgery at one side thereof and a structure of a cylindrical pipe at the other side thereof, the cylindrical pipe being provided with a lower bone cutting blade and side bone cutting blades so that the lower portion and the side surface of an alveolar bone are at the same time cut by means of drilling just one time, thereby obtaining a cylindrical autogenous bone and forming a hole for placing a tapered implant fixture, which is easier in initial fixation for the implant placement than a cylindrical implant.

BACKGROUND ART

Recently, implant surgery carried out for the placement of artificial teeth has been rapidly prevailed and considered as one of general dental surgery.

So as to conduct the implant surgery, generally, a groove into which an implant fixture is embedded is first formed on an alveolar bone by means of a drill.

If it is desired to form a hole for placing the implant fixture into the alveolar bone, since the cutting resistance is substantially high, a small hole is first formed and is expanded gradually to a large size. To do this, a plurality of drills having the same length as each other but different diameters from each other, that is, having a small diameter through a desired diameter are used sequentially to cut the alveolar bone and to form the implant placement hole.

For the purpose of removing the above-mentioned inconveniences, accordingly, there have been proposed many studies as follows:

As one example of the prior arts, there is provided Korean Patent No. 100759261 disclosing an implant drill which includes: a body having a bone accommodating portion formed at the inside thereof, in which an alveolar bone is accommodated upon the formation of a hole on the alveolar bone; a plurality of cutting blades formed on the end portion of the body and forming the hole on the alveolar bone during the rotation of the body; and a plurality of bone discharging passages formed depressedly from the surface of the body with a given angle twisted with respect to the outer periphery of the body so as to guide discharge of the bone fragments caused from the formation of the hole on the alveolar bone.

As another example of the prior arts, there is provided Korean Patent No. 100985604 disclosing a hollow drill for maxillary sinus lift which includes: a cylindrical cutting part having a hollow portion formed therein; a stopper detachably mounted on the outer periphery of the cutting part and having a hollow portion formed therein; a stopper support part disposed on one side end portion of the cutting part; and a shank part disposed on the stopper support part, wherein the cutting part has a cutting blade and a cut material discharging hole formed on the lower portion of the cutting blade and having a hollow portion communicating with the outside through the side of the cutting part, the stopper has a longitudinal length allowing the cutting blade to be exposed by a desired cutting depth, and the stopper support part has a support projection formed to prevent the stopper from being pushed in a longitudinal direction.

As another example of the prior arts, there is provided Korean Patent No. 100946269 disclosing an implant drill which includes: a punched body having a cutter disposed at one end portion thereof so as to punch an alveolar bone and a through hole formed at the other end portion thereof; and a rod body coupled to one end portion of the punched body in such a manner as to be near and separated to and from the through hole of the punched body so as to adjust the depth of the hole punched on the alveolar bone during the formation of the hole.

As yet another example of the prior arts, there is provided Korean Patent Application Laid-Open No. 10-2010-0008095 disclosing a drill for implant surgery for punching alveolar bone which includes: a body having a shape of a hollow pipe and a cutting blade formed along the end portion thereof; a connector coupled to the lower portion of the body in such a manner as to be mounted on a dental handpiece; a protruding member adapted to be inserted into the body in a state of being elastically supported against in such a manner as to be movable into and out of the body; and a stopper having a shape of a hollow pipe and adapted to be exchangeably mounted on the outer peripheral surface of the body in such a manner as to allow the body to be inserted into the alveolar bone by a given depth, the stopper having a compression part disposed at the center thereof so as to compress the stopper to a given height.

As still another example of the prior arts, there is provided Korean Patent Application Laid-Open No. 10-2009-0098428 disclosing a hollow drill for maxillary sinus lift which includes: a cutting part having a cutting blade and a cut material discharging hole formed on the lower portion of the cutting blade and having a hollow portion communicating with the outside through the side of the cutting part; a stopper having a longitudinal length allowing the cutting blade to be exposed by a desired cutting depth; and a stopper support part having a support projection formed to prevent the stopper from being pushed in a longitudinal direction.

As yet still another example of the prior arts, there is provided Korean Utility Model Registration No. 200323647 disclosing an implant drill which includes: a cylindrical body having an open portion at the bottom surface thereof; a basic blade having screw threads formed repeatedly along the outer periphery of the open portion of the body; and a vertical blade formed along the inner periphery of the body in such a manner as to be upright toward the open portion of the body.

As still another example of the prior arts, there is provided Korean Utility Model Registration No. 200230475 disclosing a drill stopper for implant surgery adapted to have a hole formed to an accurate depth at a portion where a tooth is lost, which includes: a stopper having a shape of a cylinder open at the top and bottom surface thereof, a plurality of through holes formed along the side periphery thereof so as to form a fastening portion, and a tape formed along the top portion of the lower portion thereof, so that if a hole is formed to a given depth, the stopper is gently contacted with the top surface, that is, irregular surface, of a portion from which a tooth is extracted, to prevent the hole from being formed over the given depth; and a plurality of fastening members adapted to be inserted into the fastening portion formed along the side periphery of the stopper so as to fix the stopper to a drill body.

As yet another example of the prior arts, there is provided Korean Utility Model Registration No. 20-0338095 disclosing a dental stopper drill having a chuck coupling part, a shank part, and a drill part, wherein the drill includes a stopper formed integrally thereto along the circumference thereof in a space between the shank part and the drill part in such a manner as to be protruded to a larger diameter than the shank part and the drill part, thereby allowing the drill to form a hole to a given depth.

According to the above-mentioned drills for implant surgery in the conventional practices, in the formation of a hole for placing the implant fixture into the alveolar bone, since the cutting resistance is substantially high, a small hole is first formed and is gradually expanded to a large size. As shown in FIGS. 5A to 5F, a plurality of drills having the same length as each other but different diameters from each other, that is, having a small diameter through a desired diameter are used sequentially to cut the alveolar bone and to form the implant placement hole. However, the method using the plurality of drills has some disadvantages as follows: first, since the kinds of drills and the number of drilling times are increased, the implant surgery becomes complicated and the economical load is raised; second, since the time for the implant surgery is more extended to cause the suffering experience of the patient to be severe and to also make the surgeon feel uncomfortable; third, the bone is cut to a depth of the implant placement hole to cause the amount of bone cut to be increased; fourth, the number of drills used and the manufacturing cost of the drills are all increased; and last, their durability may be weakened at the time of the repeated usage.

DISCLOSURE

Technical Problem

Accordingly, the present invention has been made in view of the above-mentioned problems occurring in the prior art, and it is an object of the present invention to provide a drill for implant surgery that is capable of cutting just marginal bone of alveolar bone by means of a lower bone cutting blade and side bone cutting blades, thereby at one time forming a hole for placing an implant fixture with the formation of a substantially low resistance and at the same time obtaining an autogenous bone therefrom.

Technical Solution

To accomplish the above object, according to a first aspect of the present invention, there is provided a drill for implant surgery, including: a drill connecting part having a drill top portion formed at one side of the top portion thereof, a drill fixing groove formed on the lower portion of the drill top portion, and a drill connecting body formed on the lower portion of the drill fixing groove; and a drilling part formed on the underside portion of the drill connecting part and having a cylindrical shape in such a manner as to be small in diameter toward the lower portion thereof and to have a space portion formed at the inside thereof, the drilling part having a plurality of side piercing portions equally spaced apart from each other along the outer periphery thereof in such a manner as to be pierced into the space portion formed at the inside thereof, a plurality of side bone cutting blades formed along one side edges of the plurality of side piercing portions, and a toothed lower bone cutting blade formed along the end periphery of the lower portion thereof.

To accomplish the above object, according to a second aspect of the present invention, there is provided a drill for implant surgery, including: a drill connecting part having a drill top portion formed at one side of the top portion thereof, a drill fixing groove formed on the lower portion of the drill top portion, and a drill connecting body formed on the lower portion of the drill fixing groove; and a drilling part formed on the underside portion of the drill connecting part and having a cylindrical shape in such a manner as to be small in diameter toward the lower portion thereof and to have a space portion formed at the inside thereof, the drilling part having a plurality of slant side piercing portions equally spaced apart from each other along the outer periphery thereof in such a manner as to be pierced into the space portion formed at the inside thereof, a plurality of slant side bone cutting blades formed along one side edges of the plurality of slant side piercing portions, and a toothed lower bone cutting blade formed along the end periphery of the lower portion thereof.

Advantageous Effect

According to the present invention, the drill for implant surgery is capable of minimizing an amount of bone cut by means of the side bone cutting blades, the lower bone cutting blade, and the central through hole, being detachably mounted on the handpiece for implant surgery in a simple manner, completing the formation of the implant placement hole at one time, additionally obtaining an autogenous bone through at least amount of bone cut to allow the amount of use of bone graft materials to be reduced, substantially decreasing the time for the implant surgery through the drilling just one time, ensuring the stability of the implant surgery, having a simple structure to improve the conveniences in use and treatment thereof, and enabling the mass production to achieve the standardization of the product and the economical prevailing thereof.

BEST MODE FOR INVENTION

According to the present invention, there is provided a drill for implant surgery that has a coupling structure to a handpiece for implant surgery at one side thereof and a structure of a cylindrical pipe at the other side thereof, the cylindrical pipe being provided with a lower bone cutting blade and side bone cutting blades so that the lower portion and the side surface of an alveolar bone are at the same time cut by means of drilling just one time, thereby obtaining a cylindrical autogenous bone and forming a hole for placing a tapered implant fixture, which is easier in initial fixation for the implant placement than a cylindrical implant.

In more detail, the drill for implant surgery according to the present invention is structured to have a drill connecting part and a drilling part formed on the underside portion of the drill connecting part, wherein the drill connecting part has a drill top portion formed at one side of the top portion thereof, a drill fixing groove formed on the lower portion of the drill top portion, and a drill connecting body formed on the lower portion of the drill fixing groove, and the drilling part has a cylindrical shape in such a manner as to be small in diameter toward the lower portion thereof and a space portion formed at the inside thereof, the drilling part having a plurality of side piercing portions equally spaced apart from each other along the outer periphery thereof in such a manner as to be pierced into the space portion formed at the inside thereof (that is, vertically with respect to a lower bone cutting blade), a plurality of side bone cutting blades formed along one side edges of the plurality of side piercing portions, and the toothed lower bone-cutting blade formed along the end periphery of the lower portion thereof.

According to the present invention, desirably, the number of side piercing portions and side bone cutting blades is 1 to 10, and more desirably, 4.

The present invention relates to the drill for implant surgery that is capable of cutting just marginal bone of alveolar bone by means of the lower bone cutting blade and the side bone cutting blades, thereby at one time forming a hole for placing an implant fixture with the formation of a substantially low resistance and at the same time obtaining an autogenous bone therefrom.

In the conventional practices, in the formation of an implant placement hole, an initial implant placement hole is first formed by means of a drill having a small diameter, and the hole is expanded to a desired size through the sequential cutting of the alveolar bone by means of drills having large diameters, thereby placing the implant fixture thereinto. According to the present invention, however, a drill having a desired diameter is first selected and coupled to a body (not shown), and after that, the body is fitted to a handpiece connected to a shaft of a surgery motor (not shown) and is fixed to a shaft connected to the motor. Next, if the alveolar bone is drilled by means of the drill, a circular groove is formed to remove the alveolar bone positioned at the inside thereof by means of tweezers therefrom, and the implant fixture is placed into the formed hole.

The removed alveolar bone, as an autogenous bone, is used as an artificial bone needed for the implant surgery.

Accordingly, the drill for implant surgery according to the present invention is used by selecting the drill having a desired diameter, coupling the drill to the drill body, fitting the drill body to the handpiece connected to the shaft of the surgery motor, fixing the drill body to the shaft connected to the motor, and drilling the alveolar bone.

Hereinafter, an explanation on the drill for implant surgery will be given with reference to the attached drawings.

Figure 1:
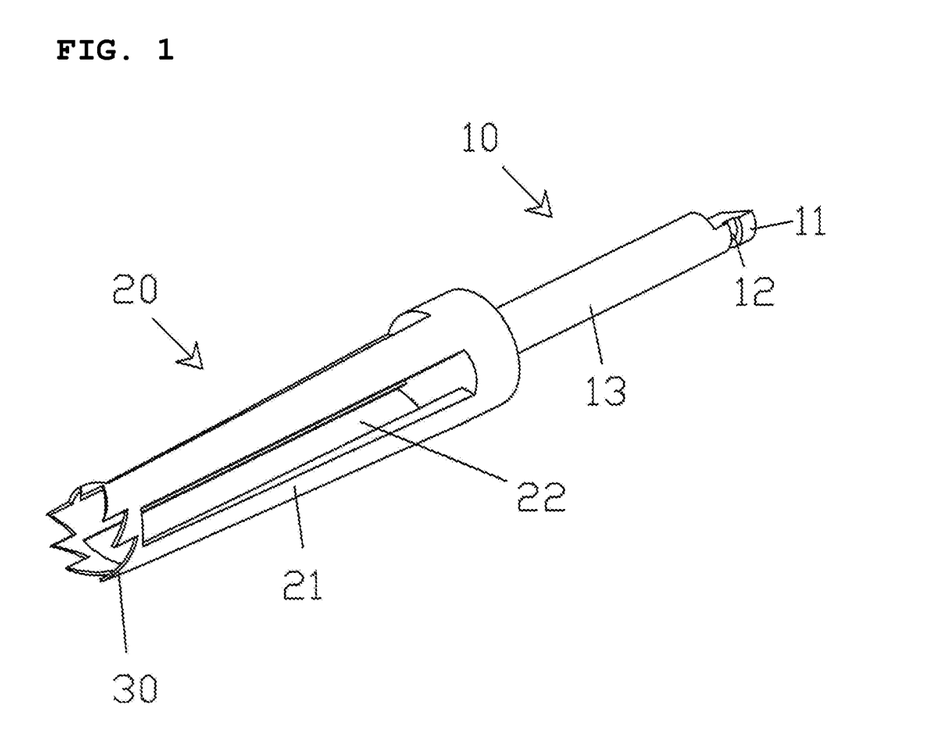
FIG. 1 is a perspective view showing the whole configuration of a drill for implant surgery according to a first embodiment of the present invention.
Figure 2:
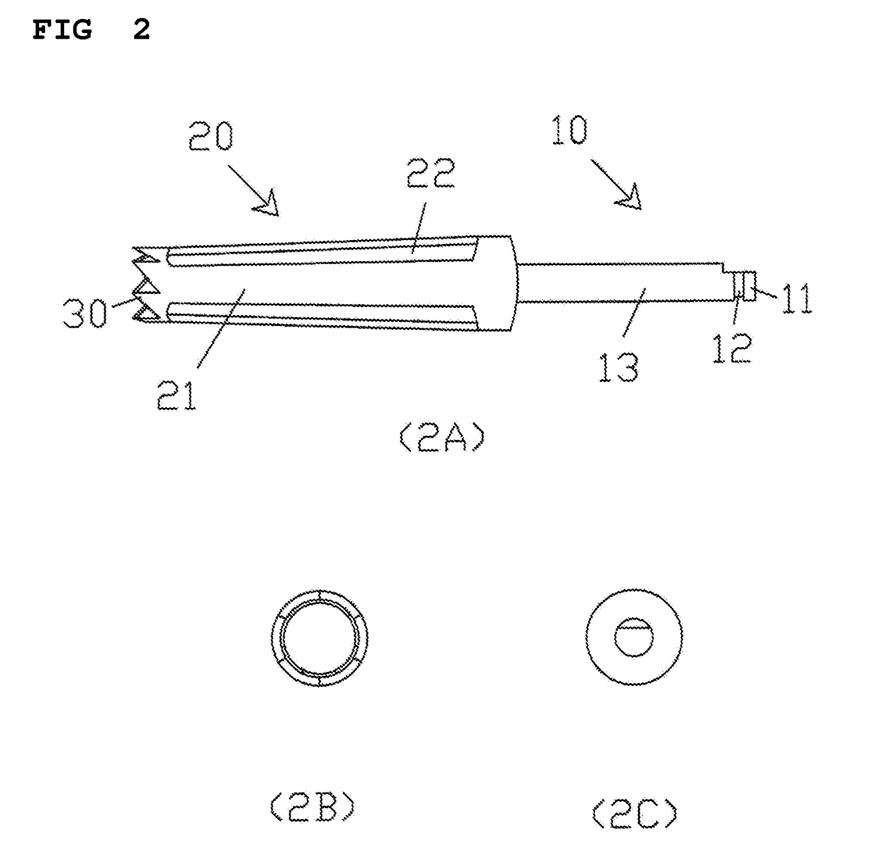
FIGS. 2A to 2C are detailed views showing the drill for implant surgery according to the first embodiment of the present invention.
Figure 3:
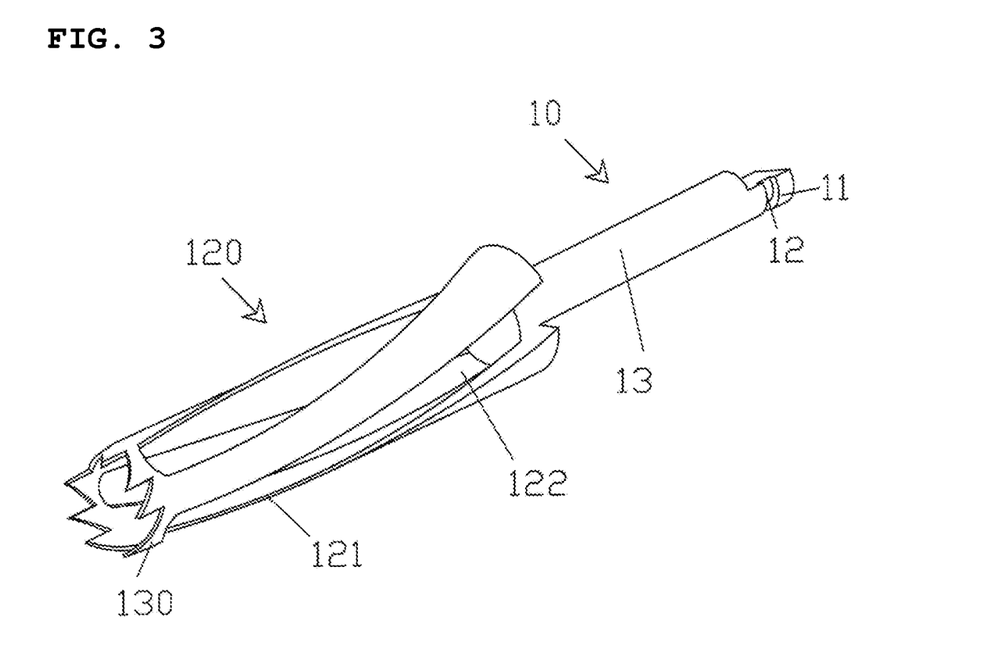
FIG. 3 is a perspective view showing a drill for implant surgery according to a second embodiment of the present invention.
Figure 4:
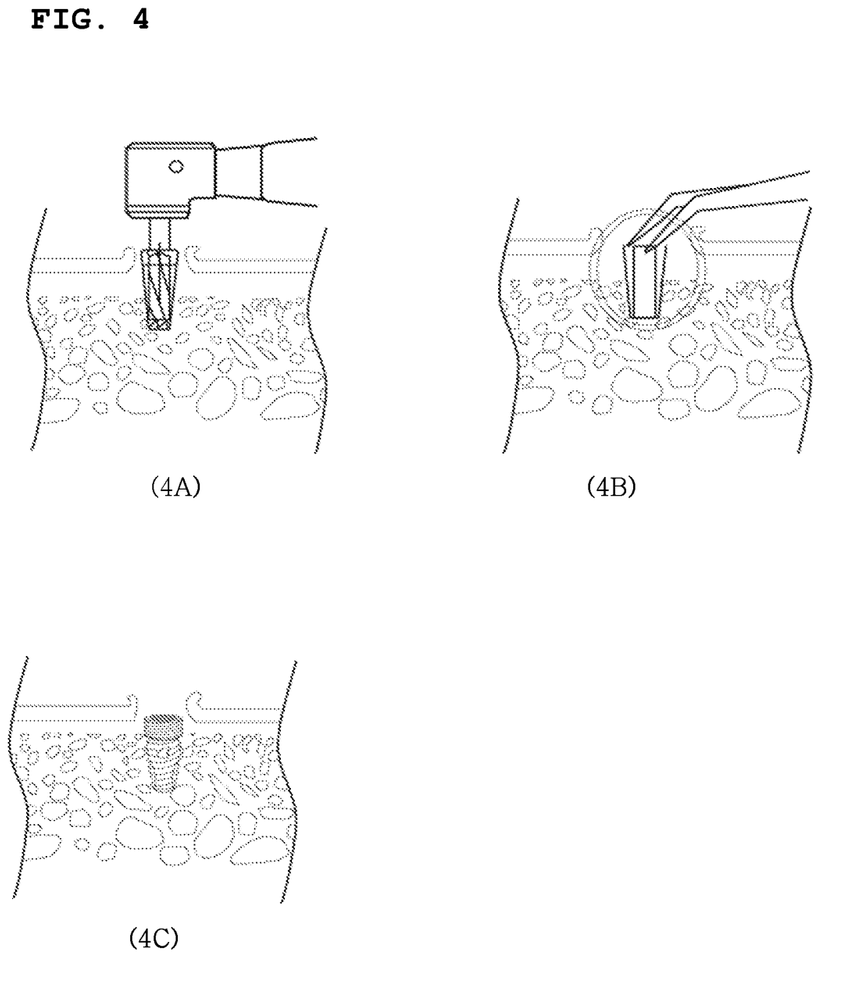
FIGS. 4A to 4C are sectional views showing the states of the use of the drill for implant surgery according to the present invention.
Figure 5:
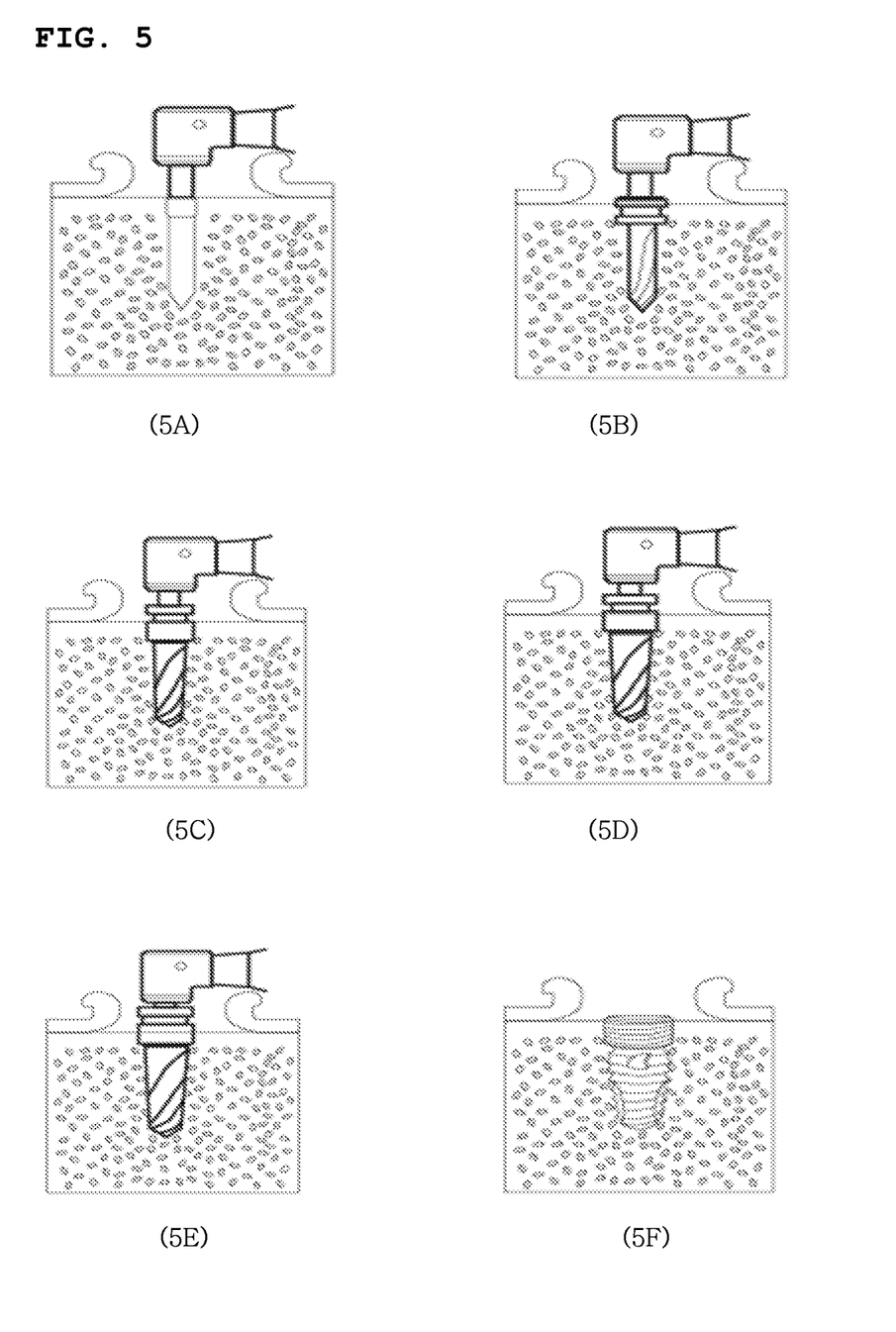
FIGS. 5A to 5F are sectional views showing the states of the use of a drill for implant surgery in conventional practices.

FIG. 1 is a perspective view showing the whole configuration of a drill for implant surgery according to a first embodiment of the present invention, FIGS. 2A to 2C are detailed views showing the drill for implant surgery according to the first embodiment of the present invention, FIG. 3 is a perspective view showing a drill for implant surgery according to a second embodiment of the present invention, FIGS. 4A to 4C are sectional views showing the states of the use of the drill for implant surgery according to the present invention, and FIGS. 5A to 5F are sectional views showing the states of the use of a drill for implant surgery in conventional practices.

According to the preferred embodiments of the present invention, a drill connecting part is denoted by a reference numeral 10, a drill top portion by 11, a drill fixing groove by 12, a drill connecting body by 13, drilling parts by 20 and 120, side bone cutting blades by 21 and 121, side piercing portions by 22 and 122, and lower bone cutting blades by 30 and 130.

As shown in FIGS. 1 to 2C, the drill for implant surgery according to the first embodiment of the present invention includes: the drill connecting part 10 and the drilling part 20 disposed on the underside of the drill connecting part 10, wherein the drill connecting part 10 has the drill top portion 11 formed at one side of the top portion thereof, the drill fixing groove 12 formed on the lower portion of the drill top portion 11, and the drill connecting body 13 formed on the lower portion of the drill fixing groove, and the drilling part 20 has a cylindrical shape in such a manner as to be small in diameter toward the lower portion thereof and to have a space portion formed at the inside thereof, the drilling part 20 having the plurality of side piercing portions 22 equally spaced apart from each other along the outer periphery thereof in such a manner as to be pierced into the space portion formed at the inside thereof (that is, to be pierced vertically with respect to the lower bone cutting blade 30), the plurality of side bone cutting blades 21 formed along one side edges of the plurality of side piercing portions 22, and the toothed lower bone cutting blade 30 formed along the end periphery of the lower portion thereof.

As shown in FIG. 3, the drill for implant surgery according to the second embodiment of the present invention includes: the drill connecting part 10 and the drilling part 20 disposed on the underside of the drill connecting part 10, wherein the drill connecting part 10 has the drill top portion 11 formed at one side of the top portion thereof, the drill fixing groove 12 formed on the lower portion of the drill top portion 11, and the drill connecting body 13 formed on the lower portion of the drill fixing groove 12, and the drilling part 120 has a cylindrical shape in such a manner as to be small in diameter toward the lower portion thereof and to have a space portion formed at the inside thereof, the drilling part 120 having the plurality of slant side piercing portions 122 equally spaced apart from each other along the outer periphery thereof in such a manner as to be pierced into the space portion formed at the inside thereof (that is, to be twistedly bent toward one side surface in the state of being vertical with respect to the lower bone cutting blade), the plurality of slant side bone cutting blades 121 formed along one side edges of the plurality of slant side piercing portions 122, and the toothed lower bone cutting blade 130 formed along the end periphery of the lower portion thereof.

Next, the assembling method of the drill for implant surgery according to the present invention will be described.

First, a drill for implant surgery having a desired diameter is selected, and then, the selected drill for implant surgery is fastened to the drill body to be activated by means of the drill top portion 11 and the drill fixing groove 12 of the drill connecting part 10. Next, the drill body is connected to the handpiece of a surgery motor, and if power is turned on, the drill for implant surgery is rotated through the rotation of the drill body. As a result, drilling is conducted to a desired depth by using the lower portion of the drill (See FIG. 4A), and next, the protrusion-shaped alveolar bone remaining at the center of the implant placement hole is removed by means of tweezers (See FIG. 4B), thereby completing the formation of the implant placement hole and conducting the implant surgery.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A drill for implant surgery, comprising:
a drill connecting part having a drill top portion, a drill fixing groove formed on a lower portion of the drill top portion, and a drill connecting body formed on a lower portion of the drill fixing groove and extending in a first direction; and
a hollow shape drilling part extending in the first direction, disposed on an underside of the drill connecting part and having a lower end portion, an upper end portion connected to and adjacent to an end portion of the drill connecting body of the drill connecting part, and a middle portion between the lower end portion and the upper end portion, and a tapered shape in such a manner as to become continuously smaller in diameter from the upper end portion of the drilling part to the lower end portion of the drilling part and to have a space portion formed at an inside of the drilling part,
wherein the drilling part includes a plurality of slant side openings equally spaced apart from each other along an outer periphery of the drilling part in such a manner as to be through into the space portion formed at the inside of the drilling part, a plurality of slant side bone cutting blades formed along side edges of the plurality of slant side openings, and a toothed lower bone cutting blade formed along an end periphery of the lower end portion of the drilling part, each of the plurality of slant side bone cutting blades being curved from the lower end portion of the drilling part toward the upper end portion of the drilling part,
wherein the end periphery of the lower end portion of the drilling part is in a closed circular shape,
wherein the toothed lower bone cutting blade includes a plurality of tooth-shaped blades formed along the closed circular shaped end periphery of the lower end portion of the drilling part,
wherein each of the plurality of side openings is a single opening which is in a closed and elongated shape and extends from an upper portion of the drilling part adjacent to the upper end portion of the drilling part to a lower portion of the drilling part adjacent to the lower end portion of the drilling part via the middle portion of the drilling part,
wherein each of the plurality of side bone cutting blades extends from the upper portion adjacent to the upper end portion of the drilling part to the lower portion adjacent to the lower end portion of the drilling part via the middle portion of the drilling part,
wherein each of the number of the side openings and the number of the side bone cutting blades is 2 to 10,
wherein the outer periphery of the drilling part becomes continuously smaller in diameter from the upper end portion of the drilling part to the lower end portion of the drilling part,
wherein the number of the plurality of tooth-shaped blades is greater than each of the number of the side openings and the number of the side bone cutting blades, and
wherein the toothed lower bone cutting blade has an inner surface and an outer surface, and each of the inner surface and the outer surface of the toothed lower bone cutting blade is in a closed circular shape when viewed from a second direction opposite to the first direction.

* * * * *